US005654177A

United States Patent [19]
Buell et al.

[11] Patent Number: 5,654,177
[45] Date of Patent: *Aug. 5, 1997

[54] PRODUCTION OF HUMAN SOMATOMEDIN C

[75] Inventors: Gary N. Buell; Nageswararao Movva, both of Geneva, Switzerland

[73] Assignee: Biogen, Inc., Cambridge, Mass.

[*] Notice: The term of this patent shall not extend beyond the expiration date of Pat. No. 5,242,811.

[21] Appl. No.: 479,006

[22] Filed: Jun. 7, 1995

Related U.S. Application Data

[60] Continuation of Ser. No. 81,979, Jun. 23, 1993, Pat. No. 5,470,721, which is a division of Ser. No. 965,047, Oct. 21, 1992, Pat. No. 5,242,811, which is a continuation of Ser. No. 496,086, Mar. 15, 1990, abandoned, which is a continuation of Ser. No. 938,170, filed as PCT/US86/00579 Mar. 25, 1986, abandoned.

[30] Foreign Application Priority Data

Mar. 26, 1985 [GB] United Kingdom ................... 8507833

[51] Int. Cl.$^6$ ........................... C12N 15/16; C12N 15/62; C12N 15/74; C12N 15/81
[52] U.S. Cl. ........................ 435/69.7; 435/69.1; 435/69.4; 435/172.3; 435/252.3; 435/252.31; 435/252.33; 435/252.34; 435/252.35; 435/320.1; 536/23.1; 536/23.4; 536/23.51
[58] Field of Search ................................ 435/69.1, 69.7, 435/69.4, 172.3, 252.3, 254.2, 252.31, 252.33, 252.34, 320.1, 252.35; 536/23.1, 23.4, 23.51

[56] References Cited

U.S. PATENT DOCUMENTS

| | | | |
|---|---|---|---|
| 4,738,921 | 4/1988 | Belagaje et al. | 435/69.7 |
| 5,019,500 | 5/1991 | Ueda et al. | 435/69.1 |
| 5,028,531 | 7/1991 | Ueda et al. | 435/69.4 |

FOREIGN PATENT DOCUMENTS

| | | |
|---|---|---|
| 123288 | 10/1984 | European Pat. Off. . |
| 128733 | 12/1984 | European Pat. Off. . |
| WO85/03949 | 9/1985 | WIPO . |
| WO87/02060 | 4/1987 | WIPO . |

OTHER PUBLICATIONS

Maniatis et al., Molecule Cloning: a Laboratory Manual, Cold Spring Harbor Laboratory, CSH, N.Y., 1982 p. 422.

J. L. Bennetzen and B.D. Hall, "Codon Selection in Yeast", *J. Biol. Chem.*, 257, pp. 3026–3031 (1981).

G. Buell et al., "Optimizing the Expression in E.coli of a Synthetic Gene Encoding Somatomedin–C (IGF–1)", *Nucleic Acids Res.*, 13, pp. 1923–1938 (1985).

L. Bülow, "Characterization Of An Artificial Bifunctional Enzyme, β–Galactosidase/galactokinase, Prepared By Gene Fusion", *Eur. J. Biochem.*, 163, pp. 443–448 (1987).

A. Carlioz et al., "Isolation of Superoxide Dismutase Mutants in *Escherichia coli*: Is Superoxide Dismutase Necessary for Aerobic Life?", *EMBO Journal*, 5(3), pp. 623–630 (1986).

M.J. Carrier et al., "High Expression of Cloned Genes in E.coli and its Consequences", *Trends Biotechnol.*, 1, pp. 109–113 (1983).

B.A. Castilho et al., "Plasmid Insertion Mutagenesis and lac Gene Fusion with Mini–Mu Bacteriophage Transposons", *J. Bacteriol.*, 158, pp. 488–495 (1984).

J.F. Delamarter et al., "Recombinant Murine GM–CSF from E. coli has Biological Activity and is Neutralized by a Specific Antiserum", *EMBO Journal*, 4, pp. 2575–2581 (1985).

D. Gheysen et al., "Systematic Alteration of the Nucleotide Sequence Preceding the Translation Initiation Codon and the Effects on Bacterial Expression of the Cloned SV40 Small–t Antigen Gene", *Gene*, 17, pp. 55–63 (1982).

R. Grantham et al., "Codon Frequencies In 119 Individual Genes Confirm Consistent Choices of Degenerate Bases According to Genome Type", *Nucleic Acids Res.*, 8, pp. 1893–1812 (1980).

E.J. Gren, "Recognition of Messenger RNA during Translational Initiation in *Escherichia coli*", *Biochimie*, 66, pp. 1–29 (1984).

H. Grosjean and W. Fiers, "Preferential Codon Usage in Prokaryotic Genes: the Optimal Codon–Anticodon Interaction Energy and the Selective Codon Usage in Efficiently Expressed Genes", *Gene*, 18, pp. 199–209 (1982).

L. Guarente et al., "Improved Methods for Maximizing Expression of a Cloned Gene: a Bacterium That Synthesizes Rabbit Beta–Globin", *Cell*, 20, pp. 543–553 (1980).

K. Hall & V. Sara, "The Somatomedin Family of Polypeptide Hormones", *Periodicum Biologorum*, 85, Supp. 1, pp. 107–114 (1983).

D. Iserentant & W. Fiers, "Secondary Structure of mRNA And Efficiency Of Translation Initiation", *Gene*, 9, pp. 1–12 (1980).

K. Itakura et al., "Chemical DNA Synthesis and Recombinant DNA Studies", *Science*, 209, pp. 1401–1405 (1980).

R.A. Jefferson, "β–Glucuronidase From *Escherichia coli* As A Gene–Fusion Marker", *Proc. Natl. Acad. Sci. USA*, 83, pp. 8447–8451 (1986).

R.J. Kaufman and P.A. Sharp, "Construction of A Modular Dihydrofolate Reductase cDNA Gene: Analysis of Signals Utilized for Efficient Expression", *Mol. Cell. Biol.*, 2(11), pp. 1304–1319 (1982).

(List continued on next page.)

*Primary Examiner*—John Le Guyader
*Attorney, Agent, or Firm*—Fish & Neave; James F. Haley, Jr.; Margaret A. Pierri

[57] ABSTRACT

A process for selecting DNA sequences that are optimal for the production of polypeptides in hosts transformed with those DNA sequences. These DNA sequences, which code for a variety of human and animal proteins, permit the high level expression of those products in host cells. In the preferred embodiment of this invention, DNA sequences optimal for the production of human somatomedin C are selected and employed to express that growth enhancing factor.

23 Claims, 3 Drawing Sheets

OTHER PUBLICATIONS

G.P. Larson et al., "*Saccharomyces cerevisiae* Actin–*Escherichia coli lacz* Gene Fusions", *Gene*, 22, pp. 31–39 (1983).

Maniatis et al., "Molecular Cloning: A Laboratory Manual", Cold Spring Harbor Laboratory, p. 426 (1982).

M.A. Peters et al., "Expression of a Biologically Active Analogue of Somatomedin-C/Insulin-Like Growth Factor I", *Gene*, 35, pp. 83–89 (1985).

E. Rinderknecht and R.E. Humbel, "Polypeptides with Non-suppressible Insulin-Like and Cell-Growth Promoting Activities in Human Serum: Isolation, Chemical Characterization, and Some Biological Properties of Forms I and II", *Proc. Natl. Acad. Sci. USA*, 73, pp. 2365–2369 (1976).

E. Rinderknecht et al., "The Amino Acid Sequence of Human Insulin-like Growth Factor I and Its Structural Homology with Proinsulin", *J. Biol. Chem.*, 253, pp. 2769–2776 (1978).

J. Smith et al., "Chemical Synthesis and Cloning of a Gene for Human β–urogastrone", *Nuc. Acids Res.*, 10, pp. 4467–4482 (1982).

J.S. Sproat and M.J. Gait, "Chemical Synthesis of a Gene For Somatomedin C", *Nucleic Acids Res.*, 13, pp. 2959–2977 (1985).

Takebe and Kaziro, "In Vitro Construction of the tufB–lacZ Fusion: Analysis of the Regulatory Mechanism of tufB Promoter", *Mol Gen Genet*, 187, pp. 355–363 (1982).

L. Tessier et al., "The Influence of mRNA Primary and Secondary Structure on Human $IFN_c$ Gene Expression in *E. coli*", *Nucleic Acids Res.*, 12, pp. 7663–7675 (1984).

M.S. Urdea et al., "Chemical Synthesis of a Gene for Human Epidermal Growth Factor Urogastrone and Its Expression in Yeast", *Proc. Natl. Acad. Sci. USA*, 80, pp. 7461–7465 (1983).

J.D. Watson et al., *Recombinant DNA: A Short Course*, pp. 176–178 (1983).

C.R. Wood, "The Influence of Messenger RNA Secondary Structure on Expression of an Immunoglobulin Heavy Chain in *Escherichia coli*", *Nucleic Acids Res.*, 12, pp. 3937–3950 (1984).

T.I. Zaghloul et al., "Translational Coupling in *Bacillus subtilis* of a Heterologous *Bacillus subtilis–Escherichia coli* Gene Fusion", *J. Bacteriol.*, 164(2), pp. 550–555 (1985).

Fragment A

```
       NcoI    AvaII          HaeII                        PstI                       HinfI                    BamHI
        +--------SMC 1-----++--------SMC X---++----SMC Y-------++-----SMC 3-----+
(5')CCATGGGTCCAGAAACCCTGTGCGGCTGTGGACGCTCGAGTTCGTGTGCCGTGACCGTGGATTCTACTTCAACAAACCGACTGGTTACGG  " 100
  1  "       "         "          "         "         "         "         "         "
(3')GGTACCCAGGTCTTTGGGACACGCCGACACCTGCGAGCTCAAGCACAGCACGGCACTGGCACCTAAGATGAAGTTGTTTGGCTGACCAATGCC
        +----------SMC 2---------++-----SMC 4------------+
A.A.   MetGlyProGluThrLeuCysGlyAlaGluLeuValAspAlaLeuGlnPheValCysGlyIleAspArgGlyPheTyrPheAsnLysProThrGlyTyrGly
```

FIG.2A

Fragment B

```
       BamHI                    HinfI/SalI                                                                        HindIII
        +--------SMC 5---------++--------SMC 6--------++------SMC 7----++-------SMC 8---------+                    222
(5')ATCCTCCTCGAGGCGTGCTCCTCAGACTGTCGACGAATCGTCGACGCTGAAATGTTGTTTCCGTTCTTTGCGACCTGAGGCGTCTAGAAATGTACTGCGCGCCGCTGAAACCGGCGAAGAGTGCATAAGCTT
101  "         "         "         "         "         "         "         "         "         "         "         "         "
(3')TAGGAGGAGCTCCGACACGAGGAGTCTGACTTAGCAGCTGCTTACACAAGGCAAGAAACGCTGGACTCCGCAGATCTTTACATGACGCGGCGACTTTGGCCGCTTCTCACGTATTCGAA
        +-----SMC 9-----++-----SMC 10-----+ +--------SMC 11----------+
A.A.   SerSerSerArgArgAlaProGlnThrGlyIleValAspGluCysCysPheArgSerCysAspLeuArgArgLeuMetTyrCysAlaProLeuLysProAlaLysSerAlaEnd
```

FIG.2B

PRODUCTION OF HUMAN SOMATOMEDIN C

This is a continuation, of application Ser. No. 08/081, 979, filed Jun. 23, 1993 now U.S. Pat. No. 5,470,721, which is a division of application Ser. No. 965,047, filed Oct. 21, 1992, now U.S. Pat. No. 5,242,811, which is a continuation of application Ser. No. 496,086, filed Mar. 15, 1990 (now abandoned), which is a continuation of application Ser. No. 938,170, filed as PCT/US86/00579 Mar. 25, 1986, (now abandoned).

TECHNICAL FIELD OF THE INVENTION

This invention relates to a process for identifying DNA sequences that are optimal for the production of any desired protein or polypeptide in hosts transformed with those DNA sequences. More particularly, it relates to the identification of those modified DNA sequences that are optimal for the production of human somatomedin C ("SMC"). This invention also relates to recombinant DNA molecules and hosts characterized by those DNA sequences, and to methods of using those DNA sequences, recombinant DNA molecules, and hosts to improve the production of human SMC and other proteins of prokaryotic and eukaryotic origin.

BACKGROUND OF THE INVENTION

Somatomedin C ("SMC") is an insulin-like growth factor that appears to be the critical protein signalling tissue growth following secretion of growth hormone from the pituitary.

The amino acid sequence of human SMC was reported by E. Rinderknecht and R. E. Humble, *J. Biol. Chem.*, 253, pp. 2769–76 (1978). It consists of a single chain polypeptide of 70 amino acids, cross-linked by three disulfide bridges. The calculated molecular weight is 7649. SMC displays extensive homology to proinsulin. For example, SMC amino acids 1 to 29 are homologous to the insulin B chain and SMC amino acids 42–62 are homologous to the insulin A chain. The connecting chain in SMC, however, shows no homology to the C peptide of proinsulin and SMC also has a C-terminal octapeptide not found in proinsulin.

SMC displays numerous growth promoting effects in vitro, such as stimulation of DNA, RNA, protein and proteoglycan synthesis [E. Rinderknecht and R. E. Humble, *Proc. Natl. Acad. Sci USA*, 73, pp. 2365–69 (1976); B. Morell and E. R. Froesch, *Eur. J. Clin. Invest.*, 3, pp. 119–123 (1973); E. R. Froesch et al., *Adv. Mental. Disord.*, 8, pp. 211–35 (1975); A. E. Zingg and E. R. Froesch, *Diabetologia*, 9, pp. 472–76 (1973); E. R. Froesch et al., *Proc. Natl. Acad. Sci. USA*, 73, pp. 2904–08 (1976)]. It also stimulates ornithine decarboxylase and cell proliferation [B. Morrel and E. R. Froesch, supra; G. K. Haselbacher and R. E. Humble, *J. Cell. Physiol.*, 88, pp. 239–46 (1976)]. In vivo, SMC stimulates growth in rats made growth-hormone deficient by hypophysectomization [E. Schoenle et al., *Nature*, 296, pp. 252–53 (1982)].

Like growth hormones, SMCs are somewhat species specific. However, SMC from one species may be biologically active in another species lower in the evolutionary scale. For example, human SMC is believed to be useful in promoting growth in cattle, swine and chickens. In laboratory animals, SMC has shown growth stimulating effects similar to those of natural human growth hormone. However, SMC is thought to be advantaged over human growth hormone because SMC is a central mediator of the growth response. Accordingly, it is a more direct regulator of growth than growth hormone.

In addition to SMC's use in treating certain forms of growth disturbances, such as dwarfism and muscle atrophy, it is also useful for stimulating tissue growth in specific areas, such as in connection with the healing of wounds, injuries and broken bones.

SMC, however, has not fulfilled its clinical potential as a tissue growth stimulator because it is available in only minute amounts through purification from human blood. Accordingly, other methods are required to overcome this lack of commercial and clinically useful quantities of SMC.

One such approach might involve the use of recombinant DNA technology to produce SMC in hosts transformed with a DNA sequence coding for it. However, this approach has not proved useful in preparing large amounts of SMC, because the expression yields of SMC in various *E. coli* hosts have been too low to provide economically useful or commercial quantities of SMC.

DISCLOSURE OF THE INVENTION

This invention solves the problems referred to above by providing a process for identifying DNA sequences that are optimal for the production of SMC, or any other desired eukaryotic or prokaryotic protein or polypeptide, in hosts transformed with those DNA sequences. She modified DNA sequences selected by this process code on expression for those proteins, particularly in the preferred embodiment of this invention, SMC, and permit the efficient high level production of them in various hosts. Accordingly, by virtue of this invention, it is for the first time possible to obtain polypeptides displaying the growth stimulating and mediating activities of SMC in clinically useful quantities.

As will be appreciated from the disclosure to follow, in the preferred embodiment of this invention, the novel DNA sequences and recombinant DNA molecules of this invention are capable of directing the production, in appropriate hosts, of large amounts of SMC and SMC-like polypeptides. These polypeptides are then useful in a wide variety of growth stimulating and mediating activities in humans, as well as in cattle, swine and chickens.

It will therefore be appreciated that one basic aspect of this invention is the design of a process for identifying DNA sequences that are optimal for the production of SMC, or any other desired eukaryotic or prokaryotic protein or polypeptide. The second basic aspect of this invention relates to various novel DNA sequences, recombinant DNA molecules and hosts that enable the production of those proteins, and particularly SMC and SMC-like polypeptides, in improved yields.

In general outline, the process of this invention for improving the production of a desired eukaryotic or prokaryotic protein or polypeptide in a host transformed with a DNA sequence encoding for that protein or polypeptide comprises the steps of replacing a DNA sequence encoding a portion of the N terminal end of an easily assayable protein or polypeptide with a degenerate series of DNA sequences encoding a portion of the N-terminal end of the desired eukaryotic or prokaryotic protein or polypeptide; expressing the resulting series of hybrid DNA sequences operatively linked to a desired expression control sequence in an appropriate host; selecting the particular hybrid DNA sequences that enable the optimal production of the easily assayable protein or polypeptide and employing those selected hybrid DNA sequences that code for the N-terminal portion of the desired polypeptide or protein in the expression of the desired polypeptide or protein. This process advantageously permits optimal production of the desired protein or polypeptide.

BRIEF DESCRIPTION OF THE DRAWINGS

FIGS. 2A and 2B depict synthetic nucleotide sequences (both strands) of two fragments—SMC A (Fragment A) (FIG. 2A) and SMC B (Fragment B) (FIG. 2B) used in one embodiment of the method of this invention to prepare a synthetic DNA sequence coding for f-Met-SMC. FIGS. 2A and 2B also display the amino acid sequences of fragments SMC A and SMC B and the various oligonucleotide sequences, 1–11, X, Y and Z, used to prepare those fragments.

BEST MODE OF CARRYING OUT THE INVENTION

Figure 1:
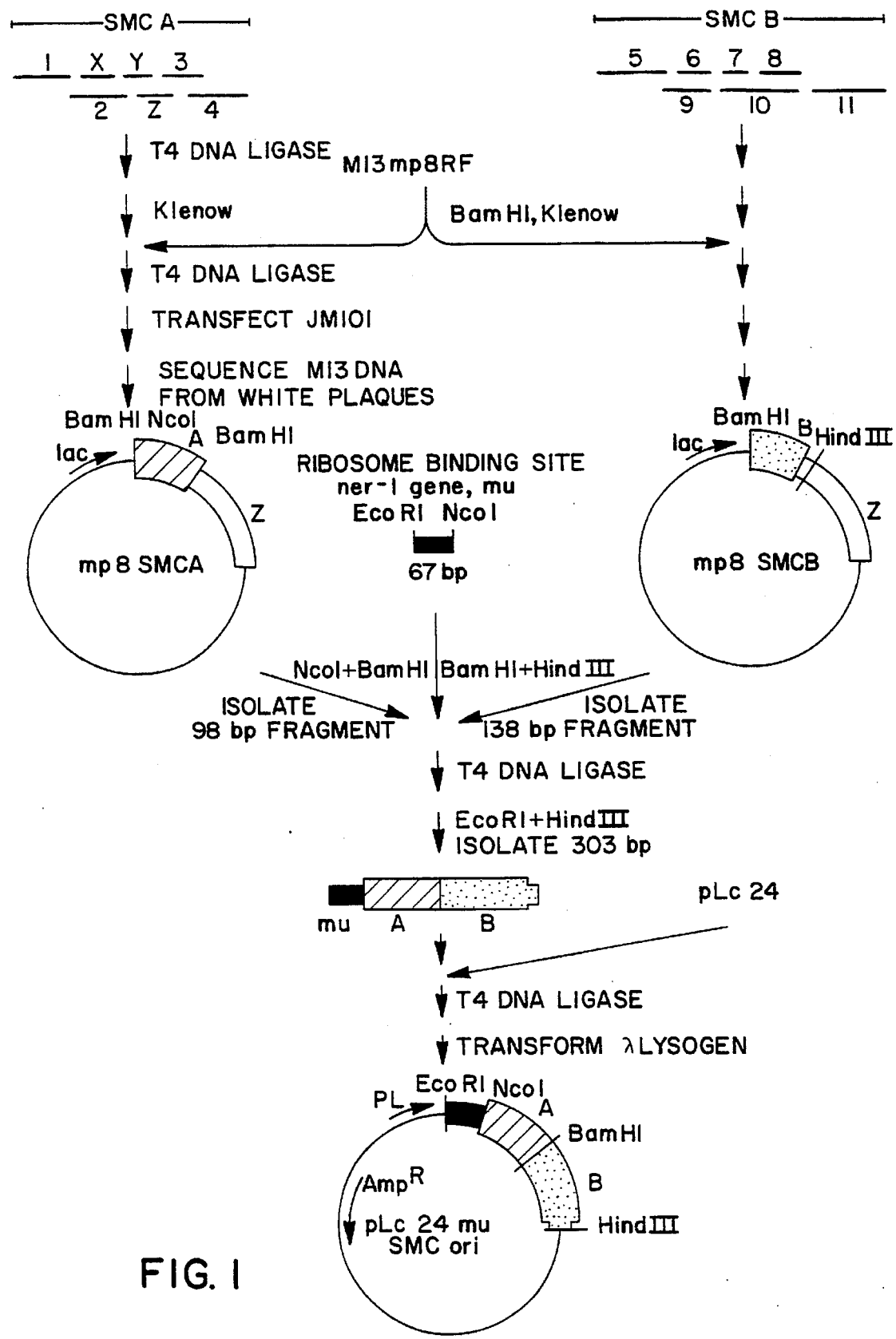
FIG. 1 displays in schematic outline one method for preparing a synthetic DNA sequence coding for f-Met-SMC and a plasmid, pLc24muSMC$_{ori}$, containing that DNA sequence downstream of sequences derived from mu and a P$_L$ promoter.

In order that the invention herein described may be fully understood, the following detailed description is set forth.

In the description, the following terms are employed:

Nucleotide

A monomeric unit of DNA or RNA consisting of a sugar moiety (pentose), a phosphate, and a nitrogenous heterocyclic base. The base is linked to the sugar moiety via the glycosidic carbon (1' carbon of the pentose). That combination of a base and a sugar is called a nucleoside. Each nucleotide is characterized by its base. The four DNA bases are adenine ("A"), guanine ("G"), cytosine ("C") and thymine ("T"). The four RNA bases are A, G, C and uracil ("U").

DNA Sequence

A linear array of nucleotides connected one to the other by phosphodiester bonds between the 3' and 5' carbons of adjacent pentoses.

Codon

A DNA sequence of three nucleotides (a triplet) which encodes through mRNA an amino acid, a translation start signal or a translation termination signal.

Gene

A DNA sequence which encodes through its template or messenger RNA ("mRNA") a sequence of amino acids characteristic of a specific polypeptide.

Transcription

The process of producing mRNA from a gene.

Translation

The process of producing a polypeptide from mRNA.

Expression

The process undergone by a DNA sequence or gene to produce a polypeptide. It is a combination of transcription and translation.

Plasmid

A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Phage or Bacteriophage

Bacterial virus many of which consist of DNA sequences encapsidated in a protein envelope or coat ("capsid").

Cloning Vehicle

A plasmid, phage DNA or other DNA sequence which is able to replicate in a host cell, which is characterized by one or a small number of endonuclease recognition sites at which such DNA sequence may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning

The process of obtaining a population of organisms or DNA sequences derived from one such organism or sequence by asexual reproduction.

Recombinant DNA Molecule or Hybrid DNA

A molecule consisting of segments of DNA from different genomes which have been joined end-to-end and have the capacity to infect some host cell and be maintained therein.

Expression Control Sequence sequence of nucleotides that controls and regulates expression of genes when operatively linked to those genes. They include the lac system, the trp system, the tac system, the trc system, major operator and promoter regions of phage A, the control region of fd coat protein, the early and late promoters of SV40, promoters derived from polyoma, adenovirus and simian virus, the promoter for 3-phosphoglycerate kinase or other glycolytic enzymes, the promoters of yeast acid phosphatase, e.g., Pho5, the promoters of the yeast α-mating factors, and other sequences known to control the expression of genes of prokaryotic or eukaryotic cells and their viruses, or combinations thereof.

SMC—SOMATOMEDIN C

SMC-Like Polypeptide

A polypeptide displaying a growth stimulating or mediating activity of SMC. For example, an SMC-like polypeptide may include an N-terminal methionine, or other peptide, fused to the first glycine of mature SMC. It may also include a threonine, instead of a methionine, at amino acid position 59. And, an SMC-like polypeptide may include various other substitutions, additions or deletions to the amino acid sequence of mature SMC.

This invention has several aspects. First, it relates to a process for improving the production of any eukaryotic or prokaryotic protein or polypeptide in a host cell transformed with a DNA sequence coding on expression for that protein or polypeptide. This invention also relates to a process for selecting DNA sequences that permit this optimal production of any eukaryotic or prokaryotic protein or polypeptide in a host cell transformed with those DNA sequences. It also relates to the DNA sequences selected by that latter process and their use in producing the proteins and polypeptides coded for by them. Finally, in one preferred embodiment, this invention relates to DNA sequences that encode SMC-like polypeptides and to processes for selecting those DNA sequences and employing them in optimizing the production of SMC in hosts transformed with them.

A wide variety of host/expression vector combinations may be utilized in our expression of both the hybrid DNA sequences of this invention and the selected DNA sequences that permit the optimal production of the desired eukaryotic or prokaryotic protein or polypeptide. For example, useful expression vectors may consist of segments of chromosomal, non-chromosomal and synthetic DNA sequences, such as various known derivatives of SV40 and known bacterial plasmids, e.g., plasmids from *E. coli* including Col El, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and Filamentous single-stranded DNA phages, vectors useful in yeasts, such as the 2μ plasmid, vectors useful in eukaryotic cells and animal cells, such as those containing SV40 derived DNA sequences, and vectors derived from combinations of plasmids and phage DNAs, such as plasmids which have been modified to employ phage DNA or other derivatives thereof.

Among such useful expression vectors are vectors that enable the expression of the cloned DNA sequences in eukaryotic hosts, such as animal and human cells (e.g., P. J. Southern and P. Berg, *J. Mol. Appl. Genet.*, 1, pp. 327–41 (1982); S. Subramani et al., *Mol. Cell. Biol.*, 1, pp. 854–64 (1981); R. J. Kaufmann and P. A. Sharp, "Amplification And Expression Of Sequences Cotransfected With A Modular Dihydrofolate Reductase Complementary DNA Gene", *J. Mol. Biol.*, (1982); R. J. Kaufmann and P. A. Sharp, "Construction of a Molecular Dihydrofolate Reductase cDNA Gene: Analysis of Signals Utilized for Efficient Expression", *Mol. Cell. Biol.*, 2(11), pp. 1304–19 (1982); S.. I. Scahill et al., "Expression And Characterization Of The Product Of A Human Immune Interferon DNA Gene In Chinese Hamster Ovary Cells", *Proc. Natl. Acad. Sci. USA*, 80, pp. 4654–59 (1983); G. Urlaub and L. A. Chasin, *Proc. Natl. Acad. Sci. USA*, 77, pp. 4216–20 (1980)).

Such expression vectors are also characterized by at least one expression control sequence that is operatively linked to the particular DNA sequence in order to control and to regulate the expression of that cloned DNA sequence. Examples of useful expression control sequences are the lac system, the trp system, the tac system, the trc system, major operator and promoter regions of phage λ, the control region of fd coat protein, the glycolytic promoters of yeast, e.g., the promoter for 3-phosphoglycerate kinase, the promoters of yeast acid phosphatase, e.g., Pho5, the promoters of the yeast α-mating factors, and promoters derived from polyoma, adenovirus and simian virus, e.g., the early and late promoters of SV40, and other sequences known to control the expression of genes of prokaryotic or eukaryotic cells and their viruses or combinations thereof.

Useful expression hosts include well known eukaryotic and prokaryotic hosts, such as strains of *E. coli*, such as *E. coli* HB101, *E. coli* X1776, *E. coli* X2282, *E. coli* DHI(λ), and *E. coli* MRC1, Pseudomonas, Bacillus, such as *Bacillus subtilis*, Streptomyces, yeasts and other fungi, animal, such as COS cells and CHO cells, and human cells and plant cells in tissue culture.

Of course, not all host/expression vector combinations function with equal efficiency in expressing the DNA sequences of this invention or in producing the polypeptides of this invention. However, a particular selection of a host/expression vector combination may be made by those of skill in the art after due consideration of the principles set forth herein without departing from the scope of this invention. For example, the selection should be based on a balancing of a number of factors. These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein.

Furthermore, within each specific expression vector, various sites may be selected for insertion of the DNA sequences of this invention. These sites are usually designated by the restriction endonuclease which cuts them. They are well recognized by those of skill in the art. It is, of course, to be understood that an expression vector useful in this invention need not have a restriction endonuclease site for insertion of the chosen DNA fragment. Instead, the vector could be joined to the fragment by alternative means. The expression vector, and in particular the site chosen therein for insertion of a selected DNA fragment and its operative linking therein to an expression control sequence, is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Various DNA sequences encoding easily assayable proteins or polpeptides may also be used in this invention. For example, in our preferred embodiment of this invention, we employ β-galactosidase because the production of that protein may be easily monitored using well-known colorimetric plating assays. We could also employ others, such as galactokinase or drug resistance genes, e.g. ampicillin resistance.

Finally, the processes of this invention and the DNA sequences selected by and used in them are applicable to any prokaryotic or eukaryotic protein or polypeptide. Among these are human and animal lymphokines, including interferons, interleukins and TNFs, human and animal hormones, including growth hormones and insulins, human and animal blood factors, including factor VIII and tPA, enzymes, antigens and other proteins and polypeptides of interest. In our preferred embodiment described herein, we used the processes of this invention to optimize the production of SMC-like polypeptides.

In order that our invention herein described may be more fully understood, the following examples are set forth. It should be understood that these examples are for illustrative purposes only and should not be construed as limiting this invention in any way to the specific embodiments recited therein.

PREPARATION OF A RECOMBINANT DNA MOLECULE HAVING A DNA SEQUENCE CODING FOR AN SMC-LIKE POLYPEPTIDE

Referring now to FIG. 1, we have shown therein a schematic outline of one embodiment of a process for preparing a recombinant DNA molecule (pLc24muSMC$_{ori}$) characterized in that it has a DNA sequence coding for human f-Met-SMC fused to a DNA sequence derived from mu and carrying a Shine Dalgarno sequence from mu, the combined DNA sequence being operatively-linked to a P$_L$ promoter derived from bacteriophage λ.

To construct pLc24muSMC$_{ori}$, we first synthesized 14 oligodeoxynucleotides (see FIGS. 1, 2A and 2B, sequences 1–11, x, Y and Z) using the reported amino acid sequence of human SMC [Rinderknecht and Humble, supra; D. G. Klapper et al., *Endocrinol.*, 112, pp. 2215–17 (1983)]. For synthesis we used the solid-phase phosphotriester method [H. Ito et al., *Nucleic Acids Res.*, 10, pp. 1755–69 (1982)]. After deprotection of the crude oligomers, we desalted them by gel filtration on Sephadex G-50 and purified them by electrophoresis on denaturing polyacrylamide preparative slab gels containing urea [T. Maniatis et al., *Biochem.*, 14, pp. 3787–94 (1975)]. We localized the bands by UV shadowing and isolated the oligodeoxynucleotides by electroelution from gel slices. We then phosphorylated the gel-purified oligodeoxynucleotides using T$_4$ polynucleotide kinase and repurified them on 15% polyacrylamide/7M urea gels, recovering the DNA by electroelution [T. Maniatis et al., *Molecular Cloning*, Cold Spring Harbor Laboratory (1982)]. Our 14 oligodeoxynucleotides varied in size from 13 to 37 bases.

In these syntheses, we considered the codon usage in highly expressed genes of *E. coli* [R. Grantham et al., *Nucleic Acids Res.*, 8, pp. 1893–1912 (1980)] and *E. coli* tRNA abundancies [T. Ikemura, *J. Mol. Biol.*, 151, pp. 389–409 (1981)]. We also included a variety of convenient endonuclease recognition sites at various positions along our oligonucleotide sequences.

We then ligated sequences 1–4 and X, Y and Z and sequences 5–11 and elongated them with Klenow polymerase to form two composite DNA sequences—Fragment A, a 98-base pair blunt-end fragment ("SMC A"), and Fragment B, a 138-base pair blunt-end fragment ("SMC B") [J. R. Rossi et al., *J. Biol. Chem.*, 257, pp. 9226–29 (1982)] (FIGS. 1, 2A and 2B). Fragment A codes for the N-terminal end of SMC and Fragment B for the remainder of SMC (FIGS. 2A and 2B).

We prepared fragment SMC A by heating 200 pmol each of sequences 1–4, X, Y and Z to 95° C. in 20 µl reannealing buffer (50 mM Tris-HCl (pH 7.6), 10 mM MgCl$_2$) and then slowly cooled the mixture to 4° C. We added dithiothreitol, ATP and T4 DNA ligase to final concentrations of 5 mM, 70 µM and 20 µ/ml, respectively, and then incubated the reaction mixture at 4° C. for 10 h. After ethanol precipitation, we applied the mixture to an 8% polyacrylamide/7M urea gel and eluted the 77- and 78-base pair strands. We then combined 25 pmol of each strand in 5 µl of reannealing buffer, heated the reaction mixture to 95° C. and slowly cooled it to 15° C. We then added dithiothreitol, dNTPs and the Klenow fragment of DNA polymerase to 5 mM, 250 µM and 2 units, respectively, and allowed the mixture to stand at room temperature for 30 min. We purified the reaction products as above and isolated 7 pmol of the 98-base pair SMC A. We prepared 20 pmole of the 138-base pair SMC B in substantially the same way using 200 pmole each of sequences 5–11.

We then inserted each of these fragments into a blunt-ended M13mp8 vector prepared by restricting 2 µg RF DNA with BamHI (for Fragment A) and with BamHI and HindIII (for Fragment B), repairing the staggered ends with 1 unit *E. coli* DNA polymerase (Klenow fragment)-in the presence of the four deoxynucleoside triphosphates (dNTPs), precipitating with ethanol, and 5'-dephosphorylating with calf intestinal phosphatase (20 units in 10 mM Tris-HCl (pH 9.2), 0.2 mM EDTA) for 30 min [J. Messing, *Methods in Enzymology*, 101, pp. 20–78 (1983)]. For ligation we used 20 ng of the linearized vector and 0.1 pmole of the DNA fragment in 10 µl ligation buffer and 40 units of T4 DNA polymerase at 15° C. for 24 h (FIG. 1).

When Fragment A was ligated to the blunt-ended M13mp8 vector, we obtained a recombinant phage that had reformed the BamHI sites at the ends of the SMC fragment; in addition an NcoI site (GGATCCATGG) had formed (mp8SMC A) (FIG. 1). When Fragment B was ligated to the double blunt-ended M13mp8. vector, we obtained a recombinant phage that had reformed the BamHI and HindIII sites at the ends of the SMC fragment (mpSSMC B) (FIG. 1).

We next transformed *E. coli* JM101 [J. Messing and J. Vieira, *Gene*, 19, pp. 269–76 (1982)] with each of these recombinant phages and plated the transformed hosts onto L-Broth plates containing 5-bromo-4-chloro-3-indolyl-β-galactopyranoside (X-GAL). We then purified phage DNA from 24 white plagues of *E. coli* JM101 transformed with mp8SMC A and mp8SMC B and sequenced the DNA by dideoxy-chain termination [A. J. H. Smith, *Methods in Enzymol.*, 65, pp. 560–80 (1980)]. We then prepared intracellular RF DNA from mp8SMC A and mp8SMC B, digested the former with NcoI/BamHI and the latter with BamHI/HindIII, and isolated the SMC-related fragments by gel electrophoresis (FIG. 1).

We then mixed the two fragments (SMC A and SMC B) with a 67-base pair fragment from the ner gene of bacteriophage mu (a gift of B. Allet) [G. Gray et al., *Gene*, 32, in press]. This fragment consists of nucleotides 1043–96 [H. Priess et al., *Mol. Gen. Genet.*, 186, pp. 315–21 (1982), FIG. 4], preceded by a EcoRI endonuclease restriction site and followed by an NcoI site (CCATGG); the internal ATG of the NcoI site forming a translation initiation codon. This fragment also contains a nearly optimal ribosomal-binding site [J. Shine and L. Dalgarno, *Nature*, 254, pp. 34–38 (1975)]. As a result of this ligation, we isolated a 303-base pair EcoRI-HindIII fragment comprising the mu gene fragment, SMC A and SMC B (FIG. 1). The ligation was such that the ATG initiation codon of the mu fragment's NcoI site was fused directly, and in the correct reading frame, to SMC A (FIGS. 1, 2A and 2B).

We introduced this fragment into pLc24 [E. Remaut et al., *Gene*, 15, pp. 81–93 (1981)], that we had previously restricted with EcoRI and HindIII, to produce plasmid pLc24muSMC$_{ori}$. This plasmid is characterized by having the SMC gene and its initiating ATG under the control of the P$_L$ promoter of bacteriophage λ (FIG. 1).

EXPRESSION OF SMC-LIKE POLYPEPTIDES USING PLASMID pLc24muSMC$_{ori}$

We cotransformed *E. coli* HB101 [T. Maniatis et al., *Molecular Cloning*, (Cold Spring Harbor Laboratory) (1982)] with pLc24muSMC$_{ori}$ and pcI857, a derivative of pACYC 184 which encodes a temperature-sensitive repressor of P$_L$ [E. Remaut et al., *Gene*, 22, pp. 103–13 (1983)]. Because the two plasmids carry different antibiotic resistance genes—penicillinase (pLc24muSMC$_{ori}$) and kanamycin (pcI857)—correctly cotransformed cultures may be selected by growth in 50 µg/ml ampicillin and 40 µg/ml kanamycin.

We inoculated 5-ml cultures in L-Broth, containing 50 µg/ml ampicillin and 40 µg/ml kanamycin, from plates containing correctly transformed *E. coli* EB101 (pLc24muSMC$_{ori}$) (pcI857) and grew the cultures overnight at 28° C. We then added 2 ml of the overnight culture to 10 ml L-Broth, prewarmed to 42° C., and vigorously agitated the cultures in a 100 ml Erlenmeyer flask at 42° C. for 2 h.

In order to assay for SMC-like polypeptide production, we centrifuged the cells from 1 ml aliquots of the culture ($A_{550}$=20) and lysed them by boiling (100° C.) for 10 min in 50 µl SDS-β-mercapto-ethanol lysis buffer [U. K. Laemmli, *Nature*, 227, pp. 680–85 (1970)]. We then assayed any SMC activity by radioimmunoassay using a commercial assay kit (Nichols Institute Diagnostics), whose standards we had previously verified with purified IGF-1 (a gift of R. Humbel). For assay we prepared our SMC containing lysates as for gel electrophoresis, diluted them at least 20-fold in the assay buffer and assayed in duplicate. We observed that human SMC, denatured under our standard lysis conditions, was as reactive in this RIA as the native hormone.

This assay demonstrated that on temperature induction, *E. coli* HB101 (pLC24muSMC$_{ori}$) (pcI857) produced very little SMC activity—1.4 µg/ml by RIA—and an amount undetectable by coomassie blue staining on protein gels. We accordingly estimated the level of SMC-like polypeptide production in that transformed host at only several hundred molecules per cell.

ATTEMPTS TO IMPROVE THE PRODUCTION OF SMC-LIKE POLYPEPTIDES

As a result of the very low levels of SMC-like polypeptide production using pLc24muSMC$_{ori}$, we attempted to construct various other plasmids having enhanced levels of expression.

In one approach, we prepared expression vectors having a DNA sequence encoding SMC fused to a DNA sequence encoding another protein. In this approach a fusion protein consisting at its amino terminal end of a non-SMC protein and at its carboxy-terminal end of an SMC-like polypeptide was produced. Although such fusion proteins could be produced in high yield from our vectors, they may be less preferred in animal and human treatment than f-met-SMC or SMC itself. As a result, for the most advantageous utilization, such fusion proteins require additional treatment to remove the non-SMC portions from them. Although such methods are available (see, e.g., U.S. Pat. Nos. 4,425,437, 4,338,397 and 4,366,246), they may be less preferred, except in the case of direct secretion and maturation, than the direct expression of a desired SMC-like polypeptide.

Accordingly, in a second approach to attempt to improve the production of SMC-like polypeptides, we adopted the deletion strategy that had proven useful in increasing the expression levels of bovine growth hormone and swine growth hormone. See, e.g., European patent applications 103,395 and 104,920. Using these methods, we prepared various modified SMC coding sequences that produced SMC-like polypeptides characterized by amino-terminal deletions. For example, we prepared expression vectors, that produced an f-Met-Δ3-SMC and an f-Met-Δ6-SMC. Although the level of production of these modified SMC's was slightly higher than the level of production of the f-Met-SMC from vector pLc24muSMC$_{ori}$, the expression levels were still very low.

Finally, in a third approach we employed various combinations of promoters and ribosome binding sites to control the expression of our SMC coding sequence. However, if anything, these modifications were worse in terms of SMC production than PLc24muSMC$_{ori}$.

SELECTION OF OPTIMAL DNA SEQUENCES CODING FOR THE PRODUCTION OF SMC-LIKE POLYPEPTIDES

Because the two approaches described previously were either unsuccessful or led to the production in many cases of a less preferred form of an SMC-like polypeptide, we decided to design an approach that might allow us to select optimal sequences coding for the production of any protein, and more particularly to select the optimal DNA sequences coding for the production of SMC-like polypeptides.

This approach was based on our hypothesis that silent mutations in the DNA sequences encoding the N-terminal portion of any gene, and in the particular embodiment described in this Example, the gene coding for f-Met-SMC, might provide improved RNA secondary structure and therefore lead to higher levels of expression in a chosen host. However, because of the many possible silent mutations that would have to be analyzed to determine what effect, if any, they might have on expression in order to select the optimal coding sequences, we needed to design a quick and simple screening method for such sequences. Without such methods, clone screening would be laborious, if not virtually impossible, and the method would fail.

Gene fusions with lacZ had been used previously to monitor the production of proteins in the absence of assays for their gene products [L. Guarente et al., *Cell,* 20, pp. 543–53 (1980); B. A. Castilho et al., *J. Bacteriol.,* 158, pp. 488–95 (1984)]. Moreover, β-galactosidase production may be easily monitored using colorimetric plating assays. Accordingly, we decided to employ this screening method to select our optimal DNA coding sequences. Of course, it should be understood that other screening methods, albeit less preferred, are also useful in selecting the optimal DNA sequences of this invention.

To vary the secondary structure of the SMC coding sequence in this illustrative embodiment of the methods of our invention, we prepared a series of synthetic linkers that comprised the 256 possible DNA sequences encoding amino acids 2–6 of SMC. Although amino acids 2–6 of SMC can be encoded by 256 different sequences, we used a 512-times degenerate linker (FIG. 3) to allow for all possible leucine codons (SMC position 5), including TTY which encodes phenylalanine. It should, of course, be understood that longer or shorter oligonucleotides could also have been used in the methods of this invention. For example, longer synthetic linkers, for example, those encoding up to SMC amino acid 20, could be usefully employed to determine the effect of those longer sequences on expression of SMC. The redundant DNA sequences of our series of 512-linkers is depicted in FIG. 3.

Figure 3:
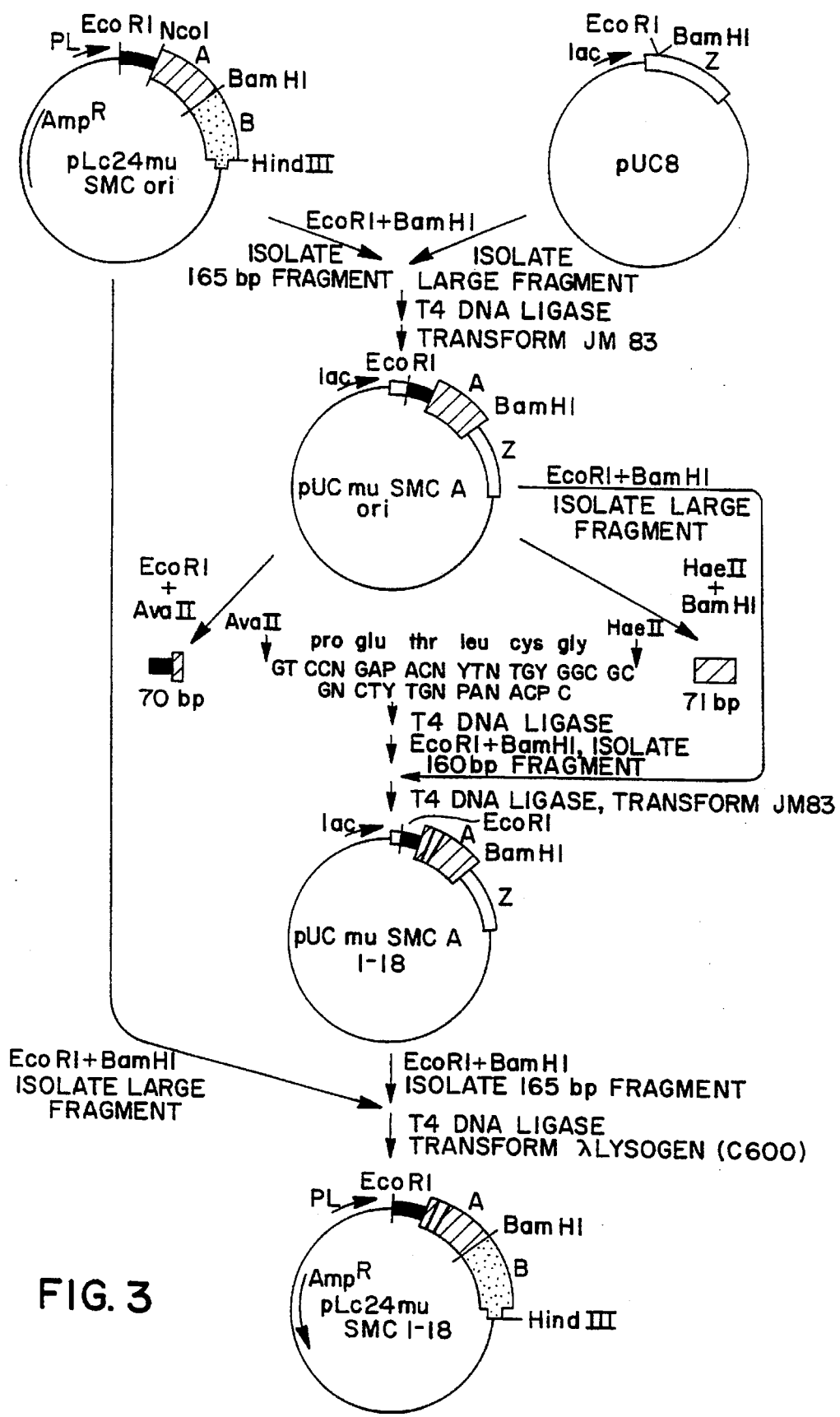
FIG. 3 displays in schematic outline one method for preparing plasmids pUCmuSMC A$_{ori}$, pUCmu-SMC A 1–18 and pLC24muSMC 1–18. In the sequence of the 512-times degenerate synthetic linker depicted in the center of FIG. 3, "N" designates all 4 base possibilities, "P" designates purines, and "Y" designates pyrimidines.

Referring now to FIG. 3, we have depicted therein one embodiment of a method of employing these redundant DNA sequences in SMC production. As displayed in FIG. 3, we first subcloned the 165-base pair EcoRI-BamHI fragment of pLc24muSMC$_{ori}$ into EcoRI-BamHI-cleaved pUC8 to produce an in-phase fusion between lacZ and SMC at the BamHI site. We designated this vector pUCmuSMCA$_{ori}$ (FIG. 3). We selected pUC8 because of its small size and its unique restriction sites which interrupt lacZ and because it can be used in a lacI host. However, it should be understood that other plasmids carrying a lacZ gene could also have been used in our screening process.

Because we made our fusion by inserting the SMC coding sequences into the promoter proximal region of the lacZ gene, expression of the hybrid gene is under the control of the lac promoter of pUC8.

Ribosomes can initiate translation in pUCmuSMCA$_{ori}$ at the lac ribosome-binding site. However, such translation will quickly terminate at the in-frame stop codons of the mu fragment derived from pLc24muSMC$_{ori}$. Alternatively, the ribosomes can initiate translation at the mu ribosome binding site to produce a fusion protein consisting of an amino-terminal portion from SMC and a carboxy-terminal portion from lacZ. The SMC-β-galactosidase fusion in pUCmuSMCA$_{ori}$ contained 35 amino acids of SMC at the N-terminus.

Although the fusion gene in pUCmuSMCA$_{ori}$ is in phase, when we transfected *E. coli* JM83 [J. Vieira and J. Messing, *Gene*, 19, pp. 259–68 (1982)] with the plasmid and cultured the transformed host on LB-agar plates containing 5-bromo- We plated 5000 colonies of *E. coli* JM83, that we had transformed with the above mixture of plasmids, onto L-Broth plates containing X-GAL. Approximately 10% of the resulting colonies were darker blue than pUCmuSMCA$_{ori}$ after 40 h at 37° C. We then analyzed 14 (both blue and white) of the 5000 colonies (*E. coli* JM83 (pUCmuSMCA 1–14)) by a variety of methods: DNA sequencing of the degenerate region, β-galactosidase enzymatic activity, and SMC expression in *E. coli* C600 [T. Maniatis et al., *Molecular Cloning* (Cold Spring Harbor Laboratory) (1982)] after substitution of the 165 bp EcoRI-BamHI fragment of each of pUCmuSMCA 1–14 into pLc24muSMC$_{ori}$. These latter plasmids are designated pLc24muSMC 1–14 in FIG. 3. Of the fourteen colonies selected for analysis, 10 were blue and 4 were white on the X-GAL plates. Table I displays the results of these various analyses:

TABLE I

| plasmid | | 2 pro. | 3 glu. | 4 thr. | 5 leu. | 6 cys | pUC8 fusion units β-gal* | pL plasmid µg/ml SMC OD$_{20}$ lysate |
|---|---|---|---|---|---|---|---|---|
| original 2-6 sequence pUCmuSMCA$_{ori}$ blue colonies | | CCA | GAA | ACC | CTG | TGC | 0.4 | 1.4 |
| pUCmuSMCA | 1 | CCC | GAA | ACT | CTG | TGT | 3.1 | 33 |
| | 2 | CCT | GAA | ACT | TTG | TGC | 2.6 | 45 |
| | 3 | CCA | GAG | ACG | TTG | TGC | 0.9 | 35 |
| | 4 | CCA | GAG | ACG | TTG | TGT | 0.9 | 43 |
| | 5 | CCT | GAA | ACT | TTG | TGT | 2.9 | 33 |
| | 6 | CCT | GAG | ACG | TTG | TGT | 1.2 | 58 |
| | 7 | CCG | GAA | ACG | TTA | TGT | 1.9 | 50 |
| | 8 | CCG | GAA | ACA | TTG | TGT | 1.2 | 65 |
| | 9 | CCA | GAA | ACG | TTG | TGT | 1.1 | 32 |
| | 10 | CCT | GAG | ACT | CTA | TGT | 2.3 | 42 |
| white colonies | | | | | | | | |
| pUCmuSMCA | 11 | CCC | GAA | ACC | CTC | TGT | <0.1 | 0.10 |
| | 12 | CCT | GAA | ACC | CTC | TGT | <0.1 | 0.11 |
| | 13 | CCG | GAA | ACC | CTC | TGT | <0.1 | 0.10 |
| | 14 | CCA | GAA | ACC | CTC | TGT | <0.1 | 0.09 |

*We assayed for β-galactosidase activity with o-nitrophenyl-β-D-galactoside (ONPG), substantially as described in J. H. Miller, Experiments in Molecular Genetics (Cold Spring Harbor Laboratories) (1972).

4-chloro-3-indolyl-β-D-galactopyranoside (X-GAL), we observed only white colonies after 16 h at 37° C. While these colonies eventually became very pale blue after 40 h; their white color after 16 h demonstrates that they were producing very little of the SMC-β-gal fusion protein. This result is, of course, consistent with our previously observed low expression level in pLc24muSMC$_{ori}$.

We then introduced into plasmid pUCmuSMCA$_{ori}$ each of our collection of 512-times degenerate synthetic DNA linkers (AvaII-HaeII fragments), encoding amino acids 2–6 of SMC as a replacement for the coding sequences for those amino acids in the original plasmid. We did not phosphorylate these linkers prior to ligation in order to avoid linker concatemers. We introduced these sequences into plasmid pUCmuSMCA$_{ori}$ by ligating each with the fragment encoding the mu ribosome binding site plus SMC amino acid 1 (the 70 bp EcoRI-AvaII fragment of pUCmuSMCA$_{ori}$) and the fragment encoding amino acids 7–32 of SMC (the 71 bp HaeII-BamHI fragment of pUCmuSMCA$_{ori}$) and then inserting the resulting EcoRI-BamHI combination fragment into EcoRI-BamHI restricted pUCmuSMCA$_{ori}$ (See FIG. 3).

As depicted in Table I, the blue colonies, containing pUCmuSMCA 1–10, produced 2.5–8 times more units of β-galactosidase than *E. coli* JM83 (pUCmuSMCA$_{ori}$). In contrast, the white colonies, containing pUCmuSMCA 11–14, produced no detectable β-galactosidase. Surprisingly, although the β-galactosidase production of pUCmuSMCA 1–10 was 2.5–8 times higher than that of the parental plasmid, when the EcoRI-BamHI fragments from these plasmids were inserted into pLc24muSMC$_{ori}$, plasmids were generated that in *E. coli* HB101 produced 23–46 times more SMC activity than the parental plasmid. There was also no apparent specific correlation between units of β-galactosidase for a given fusion and µg of SMC for the corresponding expression under P$_L$ control. However, the blue/white difference of the colonies on X-GAL plates did plainly enable the selection of DNA sequences that coded for high expressors of SMC. Accordingly, this method may be employed generally to selected optimal DNA sequences for the production of any desired eukaryotic or prokaryotic polypeptide.

While not wishing to be bound by theory, we believe that the different expression levels displayed by our degenerate DNA sequences are related to the RNA secondary structure of the nucleotides that encode the N-terminal amino acids of SMC. For example, our results indicate that the possible CCC, formed by the codons for threonine-leucine (ACN-CTN) (SMC positions 4 and 5), is particularly deleterious to SMC synthesis. All of our analyzed white colonies and pUCmuSMC$_{ori}$ were characterized by this sequence which could form hydrogen bonds with the ribosome binding site in pLc24muSMC.

Although in the embodiment of our invention described above, we employed a DNA sequence coding for our desired protein-lac Z fusion that produced a fusion protein having 35 amino acids of SMC at the N-terminal end, the relative lengths of the two parts of the fusion protein must be determined empirically for most effective screening in our method. Our experimental results have identified some of the factors that should be considered in making this choice. For example, ribosome binding site strength is important. When we used a trp ribosome-binding site instead of that from mu, our fusions that contained 35 amino acids of SMC did not produce blue colonies. The relative portions of β-galactosidase and the selected protein in the fusion protein are also important. For example, gene fusions that generated fusion proteins having only 14 SMC amino acids at the N-terminus did not allow blue/white selection. In that case, apparently the β-galactosidase activity of the fusion protein was too high to allow detection of optimal N-terminal coding sequences. Finally, the sensitivity of the detection system is important. We determined that the β-galactosidase activity range that was useful in our screening was 1–8% of the level of β-galactosidase produced by the original pUC8. With due consideration of these factors, and others that may similarly be determined as we have described above, one of skill in the art can select the appropriate fusion protein and assay for screening by the methods described herein without departing from the scope of this invention.

Although the specific SMC-like polypeptide produced in the above-illustrative example is an f-Met-SMC, it should be understood that the f-Met may be removed from the SMC by a variety of available means.

The SMC-like polypeptides produced by the methods of this invention can be formulated using conventional methods into pharmaceutically useful compositions. These compositions comprise a pharmaceutically effective amount of the SMC-like polypeptide to effect the desired tissue growth stimulation and preferably a pharmaceutically acceptable carrier. Suitable carriers are well known. As previously stated, the compositions are then useful in methods for stimulating tissue growth and in the treatment of dwarfism, muscle atrophy, broken bones, wounds or other injuries to tissue.

Microorganisms and recombinant DNA molecules prepared by the processes described herein are exemplified by cultures deposited in the culture collection Deutsche Sammlung yon Mikroorganismen in Göttingen, West Germany on Mar. 23, 1985 and identified as SMC-1 and SMC-2

SMC-1: *E. coli* HB101 (pcI857) (pLc24muSMC$_{ori}$)

SMC-2: *E. coli* HB101 (pcI857) (pLc24muSMC 8)

These cultures were assigned accession numbers DSM 3276 and 3277, respectively.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A DNA sequence encoding SMC produced by a process comprising the steps of:

(a) preparing an in-phase fusion gene comprising a DNA sequence encoding an easily assayable polypeptide and a DNA sequence encoding amino acids 2–6 of SMC, or a portion thereof, wherein the fusion gene is operatively linked to an expression control sequence, and wherein the DNA sequence encoding amino acids 2–6 of SMC incorporates codon usage bias with respect to said bacterial or yeast host;

(b) replacing a DNA sequence encoding a portion of the N-terminal end of the easily assayable polypeptide with a series of synthetic DNA sequences encoding amino acids 2–6 of SMC, each member of the series having a degenerate mutation;

(c) expressing the resulting series of mutated fusion genes in a bacterial or yeast host;

(d) selecting the particular mutated fusion genes that enable the optimal production of the assayable polypeptide;

(e) removing the DNA sequence coding for amino acids 2–6 of SMC from each of the mutated fusion genes selected in step (d); and (f) replacing a portion of a DNA sequence encoding the N-terminal end of SMC with the DNA sequence removed in step (e).

2. The DNA sequence according to claim 1, wherein said easily assayable polypeptide is selected from the group consisting of β-galactosidase, galactokinase and drug resistance markers.

3. The DNA sequence according to claim 1, wherein said expression control sequence is selected from the group consisting of the lac system, the trp system, the tac system, the trc system, the major operator and promoter regions of phage λ, the control region of fd coat protein, the early and late promoters of SV40, promoters derived from polyoma, adenovirus and simian virus, and the promoters of yeast glycolytic enzymes, α-mating factors and acid phosphatase.

4. The sequence of claim 1, wherein the step of replacing a portion of the N-terminal end of the easily assayable polypeptide with a series of synthetic DNA sequences comprises replacing with a synthetic DNA that is selected from the group consisting of all 256 possible DNA sequences encoding amino acids 2 through 6 of SMC.

5. The sequence of claim 1, wherein the step of replacing a portion of the N-terminal end of the easily assayable polypeptide with a series of synthetic DNA sequences comprises replacing with a synthetic DNA contained in the SMC coding sequence of the DNA inserts of a vector selected from the group consisting of vectors pLC24muSMC 1 through pLC24muSMC 10.

6. The sequence of claim 1, wherein the step of replacing a portion of the N-terminal end of the easily assayable polypeptide with a series of synthetic DNA sequences comprises replacing with a DNA sequence that is a 512-times degenerate linker as depicted in FIG. 3.

7. A vector having a DNA sequence according to claim 1.

8. The vector according to claim 7, wherein said DNA sequence is operatively linked to an expression control sequence in said vector.

9. The vector according to claim 8, wherein the expression control sequence is selected from the group consisting of the lac system, the trp system, the tac system, the trc system, the major operator and promoter regions of phage λ, the control region of fd coat protein, the early and late promoters of SV40, promoters derived from polyoma, adenovirus and simian virus, and the promoters of yeast glycolytic enzymes, α-mating factors and acid phosphatase.

10. A bacterial or yeast host transformed with any one of the vectors according to claim 7.

11. A process for improving the production of SMC characterized by the step of culturing a bacterial or yeast host transformed by a vector according to claim 7.

12. A process for improving the production of SMC in a bacterial or yeast host, comprising the steps of:
  (a) preparing an, in-phase fusion gene comprising a DNA sequence encoding an easily assayable polypeptide and a DNA sequence encoding amino acids 2–6 of SMC, or a portion thereof, wherein the fusion gene is operatively linked to an expression control sequence, and wherein the DNA sequence encoding amino acids 2–6 of SMC incorporates codon usage bias with respect to said bacterial or yeast host;
  (b) replacing a DNA sequence encoding a portion of the N-terminal end of the easily assayable polypeptide with a series of synthetic DNA sequences encoding amino acids 2–6 of SMC, each member of the series having a degenerate mutation;
  (c) expressing the resulting series of mutated fusion genes in said host;
  (d) selecting the particular mutated fusion genes that enable the optimal production of the easily assayable polypeptide;
  (e) removing the DNA sequence codin for amino acids 2–6 of SMC from each of the mutated fusion genes selected in step (d); and
  (f) using the DNA sequence removed in step (e) in a vector for the expression of SMC in said bacterial or yeast host.

13. The process according to claim 1, wherein said easily assayable polypeptide is selected from the group consisting of β-galactosidase, galactokinase and drug resistance markers.

14. The process according to claim 1, wherein said expression control sequence is selected from the group consisting of the lac system, the trp system, the tac system, the trc system, the major operator and promoter regions of phage λ, the control region of fd coat protein, the early and late promoters of SV40, promoters derived from polyoma, adenovirus and simian virus, and the promoters of yeast glycolytic enzymes, α-mating factors and acid phosphatase.

15. The process of claim 12, wherein the step of replacing a portion of the N-terminal end of the easily assayable polypeptide with a series of synthetic DNA sequences comprises replacing with a synthetic DNA that are selected from the group consisting of all 256 possible DNA sequences encoding amino acids 2 through 6 of SMC.

16. The process of claim 11, wherein the step of replacing a portion of the N-terminal end of the easily assayable polypeptide with a series of synthetic DNA sequences comprises replacing with a synthetic DNA contained in the SMC coding sequence of the DNA inserts of a vector selected from the group consisting of vectors pLC24muSMC 1 through pLC24muSMC 10.

17. The process of claim 11, wherein the step of replacing a portion of the N-terminal end of the easily assayable polypeptide with a series of synthetic DNA sequences comprises replacing with a DNA sequence that is a 512-times degenerate linker as depicted in FIG. 3.

18. The process of claim 12, wherein the vector in step (f) lacks a DNA sequence encoding for, upon expression, an easily assayable polypeptide.

19. A process for improving the production of an SMC polypeptide in a bacterial or yeast host, comprising the steps of:
  (a) providing a DNA sequence coding for SMC operatively linked to an expression control sequence, wherein the SMC DNA sequence incorporates codon usage bias with respect to said bacterial or yeast host;
  (b) replacing a portion of the N-terminal end of said SMC DNA sequence with a synthetic DNA sequence encoding amino acids 2–6 of SMC having one or more degenerate mutations;
  (c) transforming said bacterial or yeast host with the DNA sequence resulting from step (b);
  (d) culturing said host; and
  (e) recovering the resulting an SMC polypeptide.

20. The process of claim 19, wherein the step of replacing a portion of the N-terminal end of the SMC sequence with a synthetic DNA sequence comprises replacing with a synthetic DNA that is selected from the group consisting of all 256 possible DNA sequences encoding amino acids 2 through 6 of SMC.

21. The process of claim 19, wherein the step of replacing a portion of the N-terminal end of the SMC sequence with a synthetic DNA sequence comprises replacing with a synthetic DNA contained in the SMC coding sequence of a vector selected from the group consisting of the DNA inserts of vectors pLC24muSMC 1 through pLC24muSMC 10.

22. The process of claim 19, wherein the step of replacing a portion of the N-terminal end of the SMC sequence with a synthetic DNA sequence comprises replacing with a DNA sequence that is a 512-times degenerate linker as depicted in FIG. 3.

23. The process of claim 19, wherein the DNA sequence resulting from step (b) lacks a DNA sequence encoding for, upon expression, an easily assayable polypeptide.

* * * * *